United States Patent [19]

Welch et al.

[11] Patent Number: 5,744,666
[45] Date of Patent: Apr. 28, 1998

[54] PROCESS FOR PREPARING AN ALKYNYL FULVENE GROUP CONTAINING COMPOUND AND SAID COMPOUND

[75] Inventors: M. Bruce Welch, Bartlesville, Okla.; Bernd Peifer; Helmut G. Alt, both of Bayreuth, Germany

[73] Assignee: Phillips Petroleum Company, Bartlesville, Okla.

[21] Appl. No.: 760,886

[22] Filed: Dec. 6, 1996

Related U.S. Application Data

[62] Division of Ser. No. 434,807, May 4, 1995, Pat. No. 5,631,203.

[51] Int. Cl.$^6$ ............. C07C 13/00; C07C 45/00; C07C 15/12; C07C 13/465
[52] U.S. Cl. ............. 585/23; 585/22; 585/25; 585/26; 585/27; 585/422; 585/426; 585/429; 585/469; 585/505; 585/508; 585/534; 585/600; 585/638
[58] Field of Search ............. 585/22, 23, 25, 585/26, 27, 422, 426, 429, 505, 508, 534, 600, 638, 469

[56] References Cited

U.S. PATENT DOCUMENTS

| | | | |
|---|---|---|---|
| 3,900,512 | 8/1975 | Sih | 260/468 K |
| 4,277,495 | 7/1981 | Lacefield et al. | 424/309 |
| 4,412,088 | 10/1983 | Gruber et al. | 585/23 |
| 4,892,851 | 1/1990 | Ewen et al. | 502/104 |
| 5,308,817 | 5/1994 | Reddy et al. | 502/117 |
| 5,329,056 | 7/1994 | Belmont | 585/358 |
| 5,391,790 | 2/1995 | Rohrmann et al. | 556/28 |
| 5,449,651 | 9/1995 | Reddy et al. | 502/117 |
| 5,609,653 | 3/1997 | Roman et al. | 585/23 |

FOREIGN PATENT DOCUMENTS

| | | | |
|---|---|---|---|
| 577581 | 6/1993 | European Pat. Off. | |
| 586167 | 8/1993 | European Pat. Off. | |
| 1011429 | 12/1965 | United Kingdom | 585/25 |

OTHER PUBLICATIONS

Chem. Abst., vol. 107, 1987, p. 7820, 107:7807e, Nicolas et al.
J. Chem. Soc., Chem. Commun. 1982, 1297–98 Masuda et al.
J. Org. Chem. 1973, 38, 3588–91, Smith et al.
Inorg. Chem., 1988, 27, 3069–75, Fessler et al.
Bull. Soc. Chim. Fr. 1965, 1735–40, Gautier et al.
J. Chem. Soc. C, 1968, 606–08, Hubert et al.

*Primary Examiner*—Glenn Caldarola
*Assistant Examiner*—J. Pasterczyk
*Attorney, Agent, or Firm*—Carl D. Corvin

[57] ABSTRACT

A process for preparing an alkynyl fulvene group containing compound and said compound is provided. Said process comprises reacting an alkynyl ketone compound with a cyclopentadienyl-type compound.

12 Claims, No Drawings

5,744,666

PROCESS FOR PREPARING AN ALKYNYL FULVENE GROUP CONTAINING COMPOUND AND SAID COMPOUND

This application is a division of application Ser. No. 08/434,807 filed May 4, 1995, now U.S. Pat. No. 5,631,203.

The present invention relates to alkynyl fulvene-type compounds, alkynyl ligands, metallocene compounds, catalyst systems, processes for preparing same, and olefin polymerization processes.

BACKGROUND OF THE INVENTION

Fulvene-type compound as used herein is a compound containing a cyclopentadienyl-type group having an external carbon—carbon double bond bonding the cyclopentadienyl-type group to a hydrocarbyl group. Cyclopentadienyl-type as used herein are groups containing a cyclopentadienyl functionality, and include cyclopentadienyl, substituted cyclopentadienyl, indenyl, substituted indenyl, tetrahydroindenyl, fluorenyl, substituted fluorenyl, and octahydrofluorenyl groups. Cyclopentadienyl-type compounds are compounds containing a cyclopentadienyl-type group. The term alkynyl fulvene-type compound as defined herein is a fulvene-type compound containing a terminal alkynyl bond. As used herein, the term alkynyl ligand is a ligand containing a terminal alkynyl bond and at least one cyclopentadienyl-type group.

Cyclopentadienyl-type ligands have found a number of uses in the past. Such ligands have utility in the preparation of metallocene compounds useful for the polymerization of olefins. Other applications for metallocene compounds include asymmetric hydrogenation, alkene epoxidation, alkene isomerization, ketone reduction, and as stoichiometric reagents for stereoselective cobalt-mediated reactions, allyltitanium addition reactions with aldehydes, and the highly selective formation of allylic amines.

It would therefore be desirable to produce a variety of novel ligands from readily available materials employing a simple and economical process. It would also be desirable to produce a variety of such ligands in pure form without by-products and in high yields from readily available materials employing a simple and economical process.

Metallocene catalysts have been used in homogeneous solution polymerizations of olefins. Attempts to use soluble metallocene catalysts in a slurry or particle form type polymerization are currently not commercially feasible. It has been observed that when such particle form polymerizations are carried out in the presence of a soluble metallocene catalyst, large amounts of polymeric material are formed on the surfaces of the polymerization vessel. This surface fouling produces an adverse effect on the heat transfer and also results in the need for periodic, if not continuous, cleaning of the reactor. It would therefore be desirable to produce economical metallocene catalysts useful in polymerization processes free of reactor fouling.

For many applications, such as thermoforming, extrusion, blow molding and the production of film, it is desirable to produce a polymer having a broad molecular weight distribution. It would therefore be desirable to produce metallocene catalysts capable of producing polymers having a broad molecular weight distribution.

SUMMARY OF THE INVENTION

An object of the present invention is to provide fulvene-type compounds useful in preparing ligands.

Another object of the present invention is to provide an economical process for preparing fulvene-type compounds.

Another object of the present invention is to provide ligands useful in preparing metallocene compounds.

Another object of the present invention is to provide an economical process for preparing ligands.

Another object of the present invention is to provide metallocene compounds useful in olefin polymerizations which do not produce significant reactor fouling in a particle form polymerization process.

Another object of the present invention is to provide metallocene compounds useful in preparing polymers having a broad molecular weight distribution.

Another object of the present invention is to provide an efficient and economical process for preparing metallocene compounds.

Another object of the present invention is to provide an efficient and economical process for preparing catalyst systems.

Another object of the present invention is to provide catalyst systems useful in a variety of polymerization processes.

Still another object of the present invention is to provide a polymerization process free of significant reactor fouling, especially in particle form processes.

In accordance with the present invention, alkynyl fulvene-type compounds, alkynyl-bridged ligands, metallocene compounds, catalyst systems, processes for preparing same, and polymerization processes are provided. A process for preparing an alkynyl fulvene-type compound comprises reacting an alkynyl ketone compound with a cyclopentadienyl-type compound. A method for preparing the alkynyl-bridged ligand comprises reacting the alkynyl fulvene-type compound with an alkali metal salt of a cyclopentadienyl-type compound. The process for preparing the metallocene compound comprises reacting an alkynyl ligand, an alkali metal compound, and a transition-metal containing compound, wherein the transition metal-containing compound is represented by the formula $MX_4$ wherein M is a transition metal, and each X is individually a hydrocarbyl group containing from 1 to 20 carbon atoms, an alkoxy group containing from 1 to 12 carbon atoms, an aryloxy group containing from 6 to 20 carbon atoms, a halide, or hydride. In another embodiment the metallocene compound and a cocatalyst are combined to form a catalyst system. Other aspects of the invention include the alkynyl fulvene-type compounds, alkynyl ligands, metallocene compounds, and catalyst systems thus produced and polymerization processes employing the catalyst systems. The alkynyl fulvene-type compounds are represented by the formula QR, wherein Q is a cyclopentadienyl-type group and R is a hydrocarbyl group containing from 3 to 20 carbon atoms, wherein R is bonded to the cyclopentadienyl-type group by means of a carbon—carbon double bond, and wherein Q or R contain a terminal alkynyl bond. The alkynyl-bridged ligands are represented by the formula QRQ, wherein each Q is individually selected and is a cyclopentadienyl-type group, wherein R is a hydrocarbyl group containing from 3 to 20 carbon atoms, wherein Q or R contain a terminal alkynyl bond.

DETAILED DESCRIPTION OF THE INVENTION

Alkynyl Fulvene-type Compounds

One process for preparing the alkynyl fulvene-type compound comprises reacting an alkynyl ketone compound with a cyclopentadienyl-type compound.

The alkynyl ketone compound contains a terminal alkynyl bond and from 4 to 20 carbon atoms, preferably from 4 to 16 carbon atoms, and more preferably from 5 to 12 carbon atoms. Examples of suitable alkynyl ketones include 4-pentyn-2-one, 5-hexyn-2-one, 6-heptyn-2-one, 7-octyn-2-one, 8-nonyn-2-one, and 9-decyn-2-one.

As noted above, cyclopentadienyl-type includes substituted groups. Substituted cyclopentadienyl-type groups contain substituents which can be any substitutent which does not interfere with the reactions in the inventive process. Typical substituents include hydrocarbyl groups containing from 1 to 20 carbon atoms, alkoxy groups containing from 1 to 12 carbon atoms, silyl groups, alkyl halide groups where the alkyl contains from 1 to 12 carbon atoms, or halide. Preferably the substituents are alkyl groups containing from 1 to 20 carbon atoms or alkynyl groups containing from 3 to 20 carbon atoms, more preferably alkyl groups containing from 1 to 12 carbon atoms or alkynyl groups containing from 3 to 16 carbon atoms.

Some examples of substituents include methyl, ethyl, propyl, butyl, tert-butyl, isobutyl, amyl, isoamyl, hexyl, cyclohexyl, heptyl, octyl, nonyl, decyl, cetyl, dodecyl, 2-ethylhexyl, propenyl, butenyl, pentenyl, hexenyl, heptenyl, octenyl, propynyl, butynyl, pentynyl, hexynyl, heptynyl, octynyl, phenyl, methoxy, ethoxy, propoxy, butoxy, phenoxy, dimethylsilyl, trimethylsilyl, chloromethyl, chloroethyl, bromopropyl, chlorine, bromine, iodine, and mixtures thereof.

When reacting the alkynyl ketone and the cyclopentadienyl-type compound, generally the alkynyl ketone compound will be present in an amount in the range of from about 0.1 mole to about 20 moles per mole of cyclopentadienyl-type compound, preferably from about 0.2 mole to about 10 moles per mole, and more preferably from 0.5 moles to 5 moles per mole of cyclopentadienyl-type compound.

The reaction conditions for reacting the alkynyl ketone with the cyclopentadienyl-type compound can vary broadly depending on the particular compounds employed. Generally the temperature will be in the range of from about −78° C. to about 150° C., preferably from about 0° C. to about 125° C., and more preferably from 0° C. to 100° C.

Generally diluents are employed when reacting the alkynyl ketone with the cyclopentadienyl-type compound. Typical diluents include polar diluents such as for example tetrahydrofuran, or non-polar diluents such as alkanes, cycloalkanes, aromatic hydrocarbons, and non-cyclic ethers. Some specific examples of non-polar diluents include toluene, heptane, hexane, dichlorodimethylmethane, and diethylether.

Examples of typical fulvene-type compounds which can be prepared by the inventive process include:

9-(1-methyl(prop-2-ynylidene))fluorene,
9-(1-methyl(but-3-ynylidene))fluorene,
9-(1-methyl(pent-4-ynylidene))fluorene,
9-(1-methyl(hex-5-ynylidene))fluorene,
9-(1-methyl(hept-6-ynylidene))fluorene,
9-(1-methyl(oct-7-ynylidene))fluorene,
9-(1-methyl(non-8-ynylidene))fluorene,
(1-methyl(prop-3-ynylidene))cyclopentadiene,
(1-methyl(but-3-ynylidene))cyclopentadiene,
(1-methyl(pent-4-ynylidene))cyclopentadiene,
(1-methyl(hex-5-ynylidene))cyclopentadiene,
(1-methyl(hept-6-ynylidene))cyclopentadiene,
(1-methyl(oct-7-ynylidene))cyclopentadiene,
(1-methyl(non-8-ynylidene))cyclopentadiene,
1-(1-methyl(prop-3-ynylidene))indene,
1-(1-methyl(but-3-ynylidene))indene,
1-(1-methyl(pent-4-ynylidene))indene,
1-(1-methyl(hex-5-ynylidene))indene,
1-(1-methyl(hept-6-ynylidene))indene,
1-(1-methyl(oct-7-ynylidene))indene, and
1-(1-methyl(non-8-ynylidene))indene.

A second process for preparing the alkynyl fulvene-type compound comprises reacting an alkali metal salt of a cyclopentadienyl-type compound with a halo alkyne compound to form an alkynyl cyclopentadienyl-type compound, and then reacting the alkynyl cyclopentadienyl-type compound with a ketone containing from 3 to 12 carbon atoms, such as acetone.

The alkali metal salt of the cyclopentadienyl-type compound is prepared by reacting an alkali metal compound and a cyclopentadienyl-type compound. The alkali metal compounds employed in preparing the alkali metal salt can include any alkali metal compounds capable of forming the alkali metal salt. Typically the alkali metal compounds would be selected from the hydrocarbyl compounds of sodium, potassium, and lithium and the hydrocarbyl group would contain from 1 to 12, preferably from 1 to 8 carbon atoms.

Examples of typical alkali metal compounds include methyllithium, ethyllithium, propyllithium, butyllithium, sec-butyllithium, phenyllithium, phenylsodium, methylsodium, ethylsodium, methylpotassium, ethylpotassium, ethenyllithium, propenyllithium, butenyllithium, and mixtures thereof. The preferred alkali metal compounds are lithium alkyls. Due to availability and efficacy, butyllithium is especially preferred.

In preparing the alkali metal salt of the cyclopentadienyl-type compound, the alkali metal compound will be present in an amount in the range of from about 0.1 mole to about 20 moles per mole of cyclopentadienyl-type compound, preferably from about 1 mole to about 10 moles, more preferably from about 1.5 moles to about 5 moles, and most preferably from about 1.5 to about 2.5 moles alkali metal compound per mole of cyclopentadienyl-type compound.

The reaction conditions for preparing the alkali metal salt of the cyclopentadienyl-type compound can vary broadly depending on the particular compounds employed. Generally the temperature will be in the range of from about −78° C. to about 150° C., preferably from about 0° C. to about 125° C., and more preferably from 0° C. to 100° C.

The halo alkyne compound contains a terminal alkynyl bond and from 3 to 20 carbon atoms, preferably 3 to 16 carbon atoms, more preferably from 3 to 12 carbon atoms. Examples of suitable halo alkyne compounds include 1-chloroprop-2-yne, 1-chlorobut-3-yne, 1-chloropent-4-yne, 1-chlorohex-5-yne, 1-chlorohept-6-yne, 1-chlorooct-7-yne, 1-chloronon-8-yne, 1-chlorodec-9-yne, 1-bromoprop-2-yne, 1-bromobut-3-yne, 1-bromopent-4-yne, 1-bromohex-5-yne, 1-bromohept-6-yne, 1-bromooct-7-yne, 1-bromonon-8-yne, 1-bromodec-9-yne, 1-iodoprop- 2-yne, 1-iodobut-3-yne, 1-iodopent-4-yne, 1-iodohex-5-yne, 1-iodohept-6-yne, 1-iodooct-7-yne, 1-iodonon-8-yne, and 1-iododec-9-yne.

When reacting the halo alkyne compound and the alkali metal salt of a cyclopentadienyl-type compound, generally the halo alkyne compound will be present in an amount in the range of from about 0.1 mole to about 20 moles per mole of cyclopentadienyl-type compound, preferably from about 0.2 mole to about 10 moles per mole, and more preferably from 0.5 moles to 5 moles per mole of cyclopentadienyl-type compound.

The reaction conditions for reacting the halo alkyne compound with the alkali metal salt of a cyclopentadienyl-type compound can vary broadly depending on the particular compounds employed. Generally the temperature will be in the range of from about −78° C. to about 150° C., preferably from about 0° C. to about 125° C., and more preferably from 0° C. to 100° C.

Generally diluents are employed when reacting the halo alkyne compound with the alkali metal salt of a cyclopentadienyl-type compound. Typical diluents include polar diluents such as for example tetrahydrofuran, or non-polar diluents such as alkanes, cycloalkanes, aromatic hydrocarbons, and non-cyclic ethers. Some specific examples of non-polar diluents include toluene, heptane, hexane, dichlorodimethylmethane, and diethylether.

The alkynyl cyclopentadienyl-type compound is then reacted with the ketone to form the alkynyl fulvene-type compound.

When reacting the ketone and the alkynyl cyclopentadienyl-type compound, generally the ketone will be present in an amount in the range of from about 0.1 mole to about 20 moles per mole of cyclopentadienyl-type compound, preferably from about 0.2 mole to about 10 moles per mole, and more preferably from 0.5 moles to 5 moles per mole of cyclopentadienyl-type compound.

The reaction conditions for reacting the ketone with the cyclopentadienyl-type compound can vary broadly depending on the particular compounds employed. Generally the temperature will be in the range of from about −78° C. to about 150° C., preferably from about 0° C. to about 125° C., and more preferably from 0° C. to 100° C.

Generally diluents are employed when reacting the ketone with the cyclopentadienyl-type compound. Typical diluents include polar diluents such as for example tetrahydrofuran, or non-polar diluents such as alkanes, cycloalkanes, aromatic hydrocarbons and non-cyclic ethers. Some specific examples of non-polar diluents include toluene, heptane, hexane, dichlorodimethylmethane and diethylether.

Examples of typical fulvene-type compounds which can be prepared by the second process include:

9-(isopropylidene)-2-(prop-2-ynyl)fluorene,
9-(isopropylidene)-3-(but-3-ynyl)fluorene,
9-(isopropylidene)-3-(pent-4-ynyl)fluorene,
9-(isopropylidene)-4-(hex-5-ynyl)fluorene,
9-(isopropylidene)-2-(hept-6-ynyl)fluorene,
9-(isopropylidene)-2-(oct-7-ynyl)fluorene,
9-(isopropylidene)-2-(non-8-ynyl)fluorene,
(isopropylidene)-3-(prop-2-ynyl)cyclopentadiene,
(isopropylidene)-3-(but-3-ynyl)cyclopentadiene,
(isopropylidene)-3-(pent-4-ynyl)cyclopentadiene,
(isopropylidene)-3-(hex-5-ynyl)cyclopentadiene,
(isopropylidene)-2-(hept-6-ynyl)cyclopentadiene,
(isopropylidene)-2-(oct-7-ynyl)cyclopentadiene,
(isopropylidene)-3-(non-8-ynyl)cyclopentadiene,
1-(isopropylidene)-3-(prop-2-ynyl)indene,
1-(isopropylidene)-3-(but-3-ynyl)indene,
1-(isopropylidene)-3-(pent-4-ynyl)indene,
1-(isopropylidene)-3-(hex-5-ynyl)indene,
1-(isopropylidene)-2-(hept-6-ynyl)indene,
1-(isopropylidene)-2-(oct-7-ynyl)indene, and
1-(isopropylidene)-3-(non-8-ynyl)indene.

Alkynyl-Bridged Ligands

In another embodiment the alkynyl fulvene-type compound is reacted with an alkali metal salt of a cyclopentadienyl-type compound to produce an alkynyl-bridged ligand.

The alkali metal salt of the cyclopentadienyl-type compound is prepared by reacting an alkali metal compound and a cyclopentadienyl-type compound as described above.

When reacting the alkynyl fulvene-type compound and the alkali metal salt of the cyclopentadienyl-type compound, generally the alkynyl fulvene-type compound will be present in an amount in the range of from about 0.1 mole to about 20 moles per mole of cyclopentadienyl-type compound, preferably from about 0.2 mole to about 10 moles per mole, and more preferably from 0.5 moles to 5 moles per mole of cyclopentadienyl-type compound.

The reaction conditions for reacting the alkynyl fulvene-type compound with the alkali metal salt of the cyclopentadienyl-type compound can vary broadly depending on the particular compounds employed. Generally the temperature will be in the range of from about −78° C. to about 150° C., preferably from about 0° C. to about 125° C., and more preferably from 0° C. to 100° C.

Generally diluents are employed when reacting the alkynyl fulvene-type with the alkali metal salt of the cyclopentadienyl-type compound. Typical diluents include polar diluents such as for example tetrahydrofuran, or non-polar diluents such as alkanes, cycloalkanes, aromatic hydrocarbons, and non-cyclic ethers. Some specific examples of non-polar diluents include toluene, heptane, hexane, dichlorodimethylmethane, and diethylether.

Typical examples of alkynyl-bridged ligands where the group containing the terminal alkynyl bond is bonded to the bridging group include:

(cyclopentadienyl)(9-fluorenyl)(methyl)(prop-2-ynyl)methane,
(cyclopentadienyl)(9-fluorenyl)(methyl)(but-3-ynyl)methane,
(9-fluorenyl)(1-indenyl)(methyl)(pent-4-ynyl)methane,
(cyclopentadienyl)(9-(4-methyl)fluorenyl)(methyl)(hex-5-ynyl)methane,
(9-(1-tert-butyl)fluorenyl)(1-indenyl)(methyl)(hept-7-ynyl)methane,
(cyclopentadienyl)(1-indenyl)(methyl)(prop-2-ynyl)methane,
(cyclopentadienyl)(1-indenyl)(methyl)(but-3-ynyl)methane,
(cyclopentadienyl)(1-indenyl)(methyl)(pent-4-ynyl)methane,
(cyclopentadienyl)(9-fluorenyl)(methyl)(hex-5-ynyl)methane,
(cyclopentadienyl)(1-indenyl)(methyl)(hept-6-ynyl)methane,
bis(cyclopentadienyl)(methyl)(prop-2-ynyl)methane,
bis(cyclopentadienyl)(methyl)(but-3-ynyl)methane,
bis(fluorenyl)(methyl)(pent-4-ynyl)methane,
bis(cyclopentadienyl)(methyl)(hex-5-ynyl)methane, and
bis(1-indenyl)(methyl)(hept-6-ynyl)methane.

Examples of alkynyl-bridged ligands where the group containing the terminal alkynyl bond is bonded to the cyclopentadienyl-type ring include:

(cyclopentadienyl)(dimethyl)(9-(1-(prop-2-ynyl))fluorenyl)methane, (3-(but-3-ynyl)cyclopentadienyl)(methyl)(butyl)(9-fluorenyl)methane, (cyclopentadienyl)(dimethyl)(9-(4-(pent-4-ynyl))fluorenyl)methane, (cyclopentadienyl)(methyl)(propyl)(9-(4-(hex-5-ynyl))fluorenyl)methane, (2-(hept-7-ynyl))cyclopentadienyl)(9-(1-tert-butyl)fluorenyl)methane, (cyclopentadienyl)(dimethyl)(1-(2-(prop-2-ynyl))indenyl)methane, (3-(but-3-ynyl)cyclopentadienyl)(1-indenyl)methane, (9-(3-(but-3-ynyl)fluorenyl))(9-fluorenyl)(methyl)(pentyl)methane, (cyclopentadienyl)(dimethyl)(4-(pent-4-ynyl)cyclopentadienyl)methane, and (1-indenyl)(1-(3-(hex-5-ynyl)(1-indenyl))methane.

Metallocene Compounds

The metallocene compound comprises a ligand containing at least one cyclopentadienyl-type group bonded to a transition metal, wherein the ligand contains a terminal alkynyl bond. The metallocene compound is prepared by reacting an alkynyl ligand, an alkali metal compound, and a transition metal-containing compound. The metallocene compound produced by the inventive process is a solid polymeric product.

As noted above, the term alkynyl ligands includes ligands containing a terminal alkynyl bond and at least one cyclopentadienyl-type group. Suitable alkynyl ligands include the alkynyl-bridged ligands prepared as described above.

Other suitable alkynyl ligands can be prepared by any method known in the art. One such method is disclosed in Inorganic Chemistry, 1988, Vol. 27, 3069–75, Fessler et al. The method involves reacting butyl lithium with a cyclopentadienyl-type compound, such as indene or fluorene, followed by contact with propargyl bromide, 3-bromoprop-1-yne. The reactions can be conducted at room temperature in a diluent such as hexane. Water is added to the solution and the solution is extracted with ether. The ether solution is dried over silica gel and the ether is evaporated to recover the alkynyl ligands.

Examples of other suitable alkynyl ligands include ligands such as 1-(prop-2-ynyl)fluorene, 2-(but-3-ynyl)fluorene, 3-(pent-4-ynyl)fluorene, 4-(hex-5-ynyl)fluorene, 5-(hept-6-ynyl)fluorene, 6-(oct-7-ynyl)fluorene, 7-(non-8-ynyl)fluorene, (prop-2-ynyl)cyclopentadiene, (but-3-ynyl)cyclopentadiene, (pent-4-ynyl)cyclopentadiene, (hex-5-ynyl)cyclopentadiene, (hept-6-ynyl)cyclopentadiene, (oct-7-ynyl)cyclopentadiene, (non-8-ynyl)cyclopentadiene, (dec-9-ynyl)cyclopentadiene, 1-(prop-2-ynyl)indene, 2-(but-3-ynyl)indene, 3-(pent-4-ynyl)indene, 4-(hex-5-ynyl)indene, 5-(hept-6-ynyl)indene, 6-(oct-7-ynyl)indene, 1-(non-8-ynyl)indene, 1-(dec-9-ynyl)indene, and mixtures thereof.

The alkali metal compounds employed in preparing the metallocene compound can include any alkali metal compounds capable of forming an alkali metal salt of the alkynyl ligand. Typically the alkali metal compounds would be selected from the hydrocarbyl compounds of sodium, potassium, and lithium and the hydrocarbyl group would contain from 1 to 12, preferably from 1 to 8 carbon atoms. The preferred alkali metal compounds are lithium alkyls. Due to availability and efficacy, butyllithium is especially preferred.

The transition metal-containing compound is represented by the formula $MX_x$, wherein M is a Group IVB or VB transition metal, preferably titanium, zirconium, hafnium, or vanadium, more preferably titanium, zirconium or hafnium, x is the valence of the transition metal, and each X is individually selected from the group consisting of hydrocarbyl groups containing from 3 to 20 carbon atoms, alkoxy groups containing from 1 to 12 carbon atoms, aryloxy groups containing 6 to 12 carbon atoms, halide and hydride.

Examples of suitable X groups include methyl, ethyl, propyl, butyl, tert-butyl, isobutyl, amyl, isoamyl, hexyl, cyclohexyl, heptyl, octyl, nonyl, decyl, cetyl, dodecyl, 2-ethylhexyl, pentenyl, butenyl, phenyl, methoxy, ethoxy, propoxy, butoxy, phenoxy, chlorine, bromine, iodine, and cyclopentadienyl-type groups. Preferably X is a halide or a cyclopentadienyl-type group, more preferably X is chlorine or cyclopentadiene.

Some examples of suitable transition metal-containing compounds include, zirconium tetrachloride, zirconium tetrabromide, zirconium tetraiodide, cyclopentadienylzirconium trichloride, methylcyclopentadienylzirconium trichloride, zirconium tetramethoxide, zirconium tetraethoxide, zirconium tetrapropoxide, zirconium tetrabutoxide, pentamethylcyclopentadienylzirconium trichloride, indenylzirconium trichloride, 1-methylindenylzirconium trichloride, 1,3-indenylzirconium trichloride, hafnium tetrachloride, hafnium tetrabromide, hafnium tetraiodide, hafnium tetramethoxide, hafnium tetraethoxide, hafnium tetrapropoxide, hafnium tetrabutoxide, cyclopentadienylhafnium trichloride, indenylhafnium trichloride, titanium trichloride, titanium tetrachloride, titanium tetrabromide, titanium tetraiodide, titanium tetramethoxide, titanium tetraethoxide, titanium tetrapropoxide, titanium tetrabutoxide, cyclopentadienyltitanium trichloride, indenyltitanium trichloride, vanadium tetrachloride, vanadium tetraiodide, vanadium tetramethoxide, vanadium tetraethoxide, vanadium tetrapropoxide, and vanadium tetrabutoxide, cyclopentadienylvanadium trichloride, indenylvanadium trichloride, fluorenylvanadium trichloride, Excellent results have been obtained with zirconium tetrachloride and cyclopentadienylzirconium trichloride and they are preferred.

In preparing the metallocene compound, the alkali metal compound will be present in an amount in the range of from about 0.1 mole to about 20 moles per mole of alkynyl ligand, preferably from about 0.2 mole to about 10 moles, more preferably from about 0.5 mole to about 5 moles, and most preferably from about 0.5 mole to about 2.5 moles alkali metal compound per mole of alkynyl ligand.

Generally the transition metal-containing compound will be present in an amount in the range of from about 0.1 mole to about 50 moles per mole of alkynyl ligand, preferably from about 0.2 mole to about 20 moles per mole, and more preferably from 0.5 mole to 10 moles per mole of alkynyl ligand.

The alkynyl ligand, the alkali metal compound, and the transition metal-containing compound can be combined in any order, preferably the alkynyl ligand and the alkali metal compound are combined prior to reacting with the transition metal-containing compound. The reaction conditions for reacting the alkynyl ligand, the alkali metal compound, and the transition metal-containing compound can vary depending on the particular compounds employed. Generally the temperature will be in the range of from about −78° C. to about 150° C., preferably from about 0° C. to about 125° C., and more preferably from 0° C. to 100° C.

Generally diluents are employed when reacting the alkynyl ligand, the alkali metal compound, and the transition metal-containing compound. Typical diluents include polar diluents such as for example tetrahydrofuran, or non-polar diluents such as alkanes, cycloalkanes, aromatic hydrocarbons, and non-cyclic ethers. Some specific examples of non-polar diluents include toluene, heptane, hexane, dichlorodimethylmethane, and diethylether.

Examples of typical metallocene compounds include poly(cyclopentadienyl)(9-fluorenyl)(methyl)(prop-2-ynyl)methane zirconium dichloride, poly(2-(methyl)cyclopentadienyl)(9-fluorenyl)(methyl)(but-3-ynyl)methane zirconium dichloride, poly(2-(ethyl)cyclopentadienyl)(9-fluorenyl)(methyl)(pent-4-ynyl)methane zirconium dibromide, poly(cyclopentadienyl)(9-(4-methyl)fluorenyl)(methyl)(hex-5-ynyl)methane zirconium dichloride, poly(cyclopentadienyl)(9-(1-tert-butyl)fluorenyl)(methyl)(hept-7-ynyl)methane titanium dichloride, poly(cyclopentadienyl)(1-(2-methyl)indenyl)(methyl)(prop-2-ynyl)methane zirconium methyl chloride, poly(cyclopentadienyl)(1-indenyl)(methyl)(but-3-ynyl)methane zirconium dimethyl, poly(cyclopentadienyl)(1-indenyl)(methyl)(pent-4-ynyl)methane zirconium phenyl chloride, poly(cyclopentadienyl)(9-fluorenyl)(methyl)(hex-5-ynyl)methane zirconium phenyl chloride, poly(cyclopentadienyl)(1-indenyl)(methyl)(hept-6-ynyl)methane titanium ethyl chloride, polybis(cyclopentadienyl)(methyl)(prop-2-ynyl)methane zirconium phenyl chloride, polybis(cyclopentadienyl)(methyl)(but-3-ynyl)methane vanadium dichloride, polybis(fluorenyl)(methyl)(pent-4-ynyl)methane zirconium dibromide, polybis(cyclopentadienyl)(methyl)(hex-5-ynyl)methane titanium dibromide, polybis(indenyl)(methyl)(hept-6-ynyl)methane zirconium dichloride, poly(cyclopentadienyl)(2-(prop-2-ynyl)fluorenyl)(dimethyl)methane zirconium dichloride, poly(cyclopentadienyl)(4-(but-3-ynyl)fluorenyl)(dimethyl)methane zirconium dichloride, poly(indenyl)(2-(pent-4-ynyl)fluorenyl)(dimethyl)methane zirconium dimethyl, poly(fluorenyl)(4-(hex-5-ynyl)fluorenyl)(dimethyl)methane vanadium dichloride, poly(cyclopentadienyl)(2-(hept-6-ynyl)fluorenyl)(dimethyl)methane zirconium dimethyl, poly(indenyl)(4-(oct-7-ynyl)fluorenyl)(dimethyl)methane zirconium dipropoxide, poly(fluorenyl)(2-(non-8-ynyl)fluorenyl)(dimethyl)methane titanium dibutoxide, poly(2-(methyl)cyclopentadienyl)(1-(prop-2-ynyl)cyclopentadienyl)(dimethyl)methane vanadium dichloride, poly(1-(but-3-ynyl)cyclopentadienyl)(fluorenyl)(dimethyl)methane zirconium methyl chloride, poly(1-(pent-4-ynyl)cyclopentadienyl)(fluorenyl)(dimethyl)methane zirconium dimethyl, poly(1-(hex-5-ynyl)cyclopentadienyl)(cyclopentadienyl)(dimethyl)methane vanadium dipropyl, poly(cyclopentadienyl)(1-(prop-2-ynyl)indenyl)(dimethyl)methane zirconium dimethoxide, poly(1-(but-3-ynyl)indenyl)(fluorenyl)(dimethyl)methane zirconium dichloride, poly(1-(pent-4-ynyl)indenyl)(indenyl)(dimethyl)methane vanadium dibromide, poly(cyclopentadienyl)(1-(hex-5-ynyl)indenyl)(dimethyl)methane titanium dipropyl, poly(1-(hept-6-ynyl)indenyl)(fluorenyl)(dimethyl)methane titanium dichloride, poly(cyclopentadienyl)(2-(prop-2-ynyl)fluorenyl) zirconium dichloride, poly(cyclopentadienyl)(4-(but-3-ynyl)fluorenyl) zirconium dichloride, poly(indenyl)(2-(pent-4-ynyl)fluorenyl) zirconium dimethyl, poly(fluorenyl)(4-(hex-5-ynyl)fluorenyl) vanadium dichloride, poly(cyclopentadienyl)(2-(hept-6-ynyl)fluorenyl) zirconium dimethyl, poly(indenyl)(4-(oct-7-ynyl)fluorenyl) zirconium dipropoxide, poly(fluorenyl)(2-(non-8-ynyl)fluorenyl) titanium dibutoxide, poly(2-(methyl)cyclopentadienyl)(1-(prop-2-ynyl)cyclopentadienyl) vanadium dichloride, poly(1-(but-3-ynyl)cyclopentadienyl)(fluorenyl) zirconium methyl chloride, poly(1-(pent-4-ynyl)cyclopentadienyl)(fluorenyl) zirconium dimethyl, poly(1-(hex-5-ynyl)cyclopentadienyl)(cyclopentadienyl) vanadium dipropyl, poly(cyclopentadienyl)(3-(prop-2-ynyl)indenyl) zirconium dimethoxide, poly(1-(but-3-ynyl)indenyl)(fluorenyl) zirconium dichloride, poly(1-(pent-4-ynyl)indenyl)(indenyl) vanadium dibromide, poly(cyclopentadienyl)(2-(hex-5-ynyl)indenyl) titanium dipropyl, poly(1-(hept-6-ynyl)indenyl)(fluorenyl) titanium dichloride, and the like.

Excellent results have been obtained with poly(cyclopentadienyl)(9-(prop-2-ynyl)fluorenyl) zirconium dichloride and poly(cyclopentadienyl)(9-fluorenyl)(but-3-ynyl)(methyl)methane zirconium dichloride and they are preferred.

Catalyst Systems

Generally, cocatalysts, such as organoaluminoxanes, are employed with the metallocene compounds to produce a catalyst system. Various techniques are known for making organoaluminoxanes. One technique involves the controlled addition of water to a trialkylaluminum. Another technique involves combining a trialkylaluminum and a hydrocarbon with a compound containing water of adsorption or a salt containing water of crystallization. Many suitable organoaluminoxanes are commercially available.

Typically the organoaluminoxanes comprise oligomeric, linear and/or cyclic hydrocarbyl aluminoxanes having repeating units of the formula

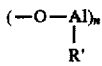

wherein each R' is a hydrocarbyl group, preferably an alkyl group containing 1–8 carbon atoms, n is 2 to 50, preferably 4 to 40, more preferably 10 to 40. Typically R' is predominantly methyl or ethyl. Preferably at least about 30 mole percent of the repeating groups have an R' which is methyl, more preferably at least 50 mole percent, and still more preferably at least 70 mole percent. Generally in the preparation of an organoaluminoxane, a mixture of linear and cyclic compounds is obtained. Organoaluminoxanes are commercially available in the form of hydrocarbon solutions, generally aromatic hydrocarbon solutions.

Typically such organoaluminoxane solutions contain trialkylaluminum compounds as well as the oligomeric organoaluminoxane. The trialkylaluminum compounds generally include those in which the alkyl groups contain from 1 to 12 carbon atoms, preferably from 1 to 8 carbon atoms.

A solid organoaluminoxy product can be prepared by reacting an organoaluminoxane and an oxygen-containing compound selected from the group consisting of organo boroxines, organic boranes, organic peroxides, alkylene oxides, and organic carbonates. Organo boroxines are preferred.

The amount of organoaluminoxane relative to the metallocene compound can vary broadly depending upon the particular catalyst selected and the results desired. Typically, the organoaluminoxane will be present in the amount of about 0.1 mole to about 10,000 moles per mole of metallocene compound, preferably about 1 moles to about 5,000 moles, and more preferably 5 moles to 1,000 moles.

Other cocatalysts can also be employed in the catalyst systems. Examples of suitable cocatalysts include any of those organometallic cocatalysts which have in the past been employed in conjunction with transition metal-containing olefin polymerization catalysts. Some typical examples include organometallic compounds of metals of Groups IA, IIA, and IIIB of the Periodic Table. Examples of such compounds include organometallic halide compounds, organometallic hydrides, and metal hydrides. Some specific examples include triethylaluminum, tri-isobutylaluminum, diethylaluminum chloride, diethylaluminum hydride, and the like. Other examples of known cocatalysts include the use of compounds capable of forming a stable non-coordinating counter anion, such as disclosed in U.S. Pat. No. 5,155,080, e.g. using triphenyl carbenium tetrakis (pentafluorophenyl)boronate or tris(pentaflurophenyl)boron. Another example would be the use of a mixture of trimethylaluminum and dimethylfluoroaluminum such as disclosed by Zambelli et. Macromolecules, 22, 2186 (1989).

Polymerization Processes

The catalyst system is useful in the polymerization of olefin compounds. The catalyst system is contacted with at least one olefin under polymerization conditions. A variety of olefin compounds are suitable for use as monomers in the polymerization process of the present invention. Olefins which can be employed include aliphatic linear, branched, cyclic, and aromatic olefins. Olefins having 2 to 24 carbon atoms are most often used, preferably 2 to 18 carbon atoms. Ethylene and propylene are especially preferred. Often a second or third such olefin (comonomer) is employed. Typical polymerizable olefins include ethylene, propylene, 1-butene, 1-pentene, 3-methyl-1-butene, 4-methyl-1-pentene, 1-hexene, 2-hexene, cyclohexene, 1-heptene, 1-octene, styrene, cyclopentene, cyclooctene, norbornene, tetracyclododecene, methyltetracyclododecene, dienes such as 1,3-butadiene, and mixtures thereof.

The reaction conditions for contacting the olefin and the catalyst system can vary broadly depending on the olefin employed, and are those sufficient to polymerize the olefins. Generally the temperature is in the range of about 20° C. to about 300° C., preferably in the range of 50° C. to 150° C. The pressure is generally in the range of from about 0.5 MPa to about 10.0 MPa (70–1500 psi).

The polymerization processes according to the present invention can be performed either batchwise or continuously. The olefin, metallocene compound, and cocatalyst can be contacted in any order. A diluent such as isobutane is generally employed. The reactor is heated to the desired reaction temperature and olefin, such as ethylene, is then admitted and maintained at a partial pressure within a range of from about 0.5 MPa to about 5.0 MPa (70–725 psi) for best results. Hydrogen can be employed to control the molecular weight of the polymer. At the end of the designated reaction period, the polymerization reaction is terminated and the unreacted olefin and diluent can be vented. The reactor can be opened and the polymer can be collected as a free-flowing white solid and dried to obtain the product.

The olefin polymers produced with the present invention are useful in preparing articles prepared by conventional polyolefin processing techniques, such as injection molding, rotational molding, film extrusion, pipe extrusion, and blow molding.

The following examples will serve to show the present invention in detail by way of illustration and not by way of limitation.

EXAMPLE 1

The alkynyl ligand 9-(prop-2-ynyl)fluorene was prepared by reacting fluorenyllithium and 3-bromoprop-1-yne. Fluorenyllithium was prepared by reacting 5.00 g (30.08 mmol) fluorene dissolved in 100 mL diethyl ether with 18.80 mL (30.08 mmol) n-butyllithium (1.6M in hexane) at room temperature while stirring slowly. The orange solution was stirred for at least four hours at room temperature and then cooled to −78° C. Then 30.08 mmol 3-bromo-1-propyne was added dropwise. The reaction mixture was stirred overnight at room temperature and then hydrolyzed with 50 mL water. The organic phase was dried over sodium sulfate, and the solvent was evaporated in a vacuum. The residue was taken up in n-pentane and filtered over silica gel. The solvent was evaporated in a vacuum. The fluorene derivative 9-(prop-2-ynyl)fluorene was precipitated as light yellow to colorless oil. The yield was 90 to 95%.

A metallocene compound was prepared by reacting 9-(prop-2-ynyl)fluorenyllithium with cyclopentadienylzirconium trichloride. The 9-(prop-2-ynyl)fluorenyllithium was prepared by reacting 1.00 g (4.90 mmol) 9-(prop-2-ynyl)fluorene and 3.06 mL (4.90 mmol) n-butyllithium (1.6M in hexane) in 50 mL diethyl ether at room temperature. The reaction mixture was stirred for 5 hours and then 1.29 g (4.90 mmol) cyclopentadienylzirconium trichloride was added. The reaction mixture was stirred overnight. The black precipitate solid was filtered and washed twice with 50 mL n-pentane. The thus produced metallocene compound (cyclopentadienyl)(9-(prop-2-ynyl)fluorenyl)zirconium dichloride was extracted with 50 mL methylene chloride. The solvent was removed under vacuum.

A catalyst system was prepared by mixing together 0.11 g metallocene compound and trimethylaluminum treated 948 Davison Silica. To the mixture was added 20 mL Schering methylaluminoxane (1.1M). The mixture was stirred for 1 hour. The solid was washed and filtered 2 times with 25 mL hexane. The thus produced catalyst system was dried under vacuum to yield 2.901 g.

Ethylene was polymerized in a 1-gallon stirred autoclave reactor under particle form conditions employing 0.4320 g of the thus prepared catalyst system in 2 liter isobutane. The polymerization was conducted at a temperature of 90° C., a total pressure of 450 psig, in the presence of hydrogen for one hour. After the polymerization was complete, the isobutane was removed and the polymer collected as a dry fluff. The polymer yield was 21.2 g. The polymer density was 0.9823 g/cc measured according to ASTM D 1505. The number average molecular weight determined by gel permeation chromatography was 5,150. The weight average molecular weight determined by gel permeation chromatography was 39,000. The heterogeneity index was 7.63. Similar runs employing 0.0918 g and 0.2190 g of the catalyst system produced a small amount of polymer.

EXAMPLE 2

The alkynyl fulvene-type compound 6-(but-3-ynyl)-6-methylfulvene, was prepared by reacting 5-hexyn-2-one with cyclopentadiene. To a solution of 2.54 g (26.43 mmol) 5-hexyne-2-one and 5.45 mL (66.08 mmol) cyclopentadiene in 20 mL methanol was added at 0° C. 3.28 mL (39.65 mmol) pyrrolidine. The reaction mixture was allowed to come to room temperature and was stirred for 5 hours. Then 4.0 mL (69.94 mmol) glacial acetic acid, 100 mL water and 50 mL n-pentane were added. The organic phase was dried over sodium sulfate and filtered over silica gel. The solvent was evaporated under vacuum. The yield was 3.40 g yellow oil, (23.58 mmol), 89% (based on the ketone) of the thus produced alkynyl fulvene-type compound 6-(but-3-ynyl)-6-methylfulvene.

The alkynyl-bridged ligand (cyclopentadienyl)(9-fluorenyl)(but-3-ynyl)(methyl)methane was prepared by reacting the alkynyl fulvene compound and fluorenyllithium. Fluorenyllithium was prepared by reacting fluorene and n-butyllithium. To a solution of 3.50 g (21.06 mmol) fluorene in 80 mL diethyl ether was slowly added at room temperature, 13.16 mL (21.06 mmol) n-butyllithium (1.6M in hexane). The reaction mixture was stirred overnight. Then 3.04 g (21.06 mmol) 6-(but-3-ynyl)-6-methylfulvene was added and the reaction mixture was stirred for 60 minutes. The reaction mixture was hydrolyzed with 50 mL water. The organic phase was separated and the solvent was removed in vacuo. The residue was dissolved in n-pentane. The solution was dried over sodium sulfate and filtered over silica gel. White crystals were formed at −25 ° C. to yield 5.59 g (18.01 mmol) of the thus produced alkynyl bridged ligand (cyclopentadienyl)(9-fluorenyl)(but-3-ynyl)(methyl)methane.

A metallocene compound was prepared by reacting the alkynyl-bridged ligand (cyclopentadienyl)(9-fluorenyl)(methyl)(but-3-ynyl)methane with two equivalents of n-butyllithium and then zirconium tetrachloride to produce a black polymeric product. To a solution of 1.50 g (4.83 mmol) (cyclopentadienyl)(9-fluorenyl)(methyl)(but-3-ynyl) methane in 100 mL diethyl ether was slowly added 6.04 mL (9.66 mmol) n-butyllithium (1.6M in hexane) at room temperature. The reaction mixture was stirred overnight. The black precipitate was filtered and washed twice with 50 mL n-pentane each. The thus produced metallocene compound (cyclopentadienyl)(9-fluorenyl)(but-3-ynyl)(methyl)methane zirconium dichloride was extracted with 50 mL methylene chloride and the solvent was removed under vacuum.

A catalyst system was prepared by mixing together 0.11 g metallocene compound and trimethylaluminum treated 948 Davison Silica. To the mixture was added 20 mL Schering methylaluminoxane (1.1M in toluene). The mixture was stirred for 1 hour. The solid was washed and filtered 2 times with 25 mL hexane. The thus produced catalyst system was dried under vacuum to yield 2.949 g.

Ethylene was polymerized in a 1-gallon stirred autoclave reactor under particle form conditions employing 0.4520 g of the thus prepared catalyst system in 2 liter isobutane. The polymerization was conducted at a temperature of 90° C., a total pressure of 450 psig, in the presence of hydrogen for one hour. After the polymerization was complete, the isobutane was removed and the polymer collected as a dry fluff. The polymer yield was 4.6 g. The polymer density was 1.0102 g/cc measured according to ASTM D 1505. The number average molecular weight determined by gel permeation chromatography was 8,210. The weight average molecular weight determined by gel permeation chromatography was 124,000. The heterogeneity index was 15.11.

That which is claimed is:

1. A process for preparing an alkynyl fulvene group containing compound comprising reacting an alkynyl ketone compound with a cyclopentadienyl-type compound to produce the alkynyl fulvene group containing compound:

wherein the alkynyl ketone compound contains a terminal alkynyl group and from 4 to 20 carbon atoms; and wherein the cyclopentadienyl-type compound is a compound containing a cyclopentadienyl-type group, wherein the cyclopentadienyl-type group is a cyclopentadienyl, substituted cyclopentadienyl, indenyl, substituted indenyl, tetrahydroindenyl, fluorenyl, substituted fluorenyl, or octahydrofluorenyl group, and wherein the substituents are hydrocarbyl groups containing from 1 to 20 carbon atoms, alkoxy groups containing from 1 to 12 carbon atoms, silyl groups, alyl halide groups where the alkyl contains from 1 to 12 carbon atoms, or halide.

2. A process according to claim 1 wherein said alkynyl ketone compound is selected from the group consisting of 4-pentyn-2-one, 5-hexyn-2-one, 6-heptyn-2one, 7-octyn-2-one, 8-nonyn-2-one, and 9-decyn-2-one.

3. A process according to claim 1 wherein said substituents are selected from the group consisting of methyl, ethyl, propyl, butyl, tertbutyl, isobutyl, amyl, isoamyl, hexyl, cyclohexyl, heptyl, octyl, nonyl, decyl, cetyl, dodecyl, 2-ethylhexyl, propenyl, butenyl, pentenyl, hexenyl, heptenyl, octenyl, propynyl, butynl, pentynyl, hexynyl, heptynyl, octynyl, phenyl, methoxy, ethoxy, propoxy, butoxy, phenoxy, dimethylsilyl, trimethylsilyl chloromethyl, chloroethyl, bromopropyl, chlorine, bromine, iodine, and mixtures thereof.

4. A process according to claim 1 wherein said alkynyl fulvene group containing compound is selected from the group consisting of 9-(1-methyl(prop-2-ynylidene))fluorene, 9-(1-methyl(but-3-ynylidene))fluorene, 9-(1-methyl(pent-4-ynylidene))fluorene, 9-(1-methyl(hex-5-ynylidene))fluorene, 9-(1-methyl(hept-6-ynylidene))fluorene, 9-(1-methyl(oct-7-ynylidene))fluorene, 9-(1-methyl(non8-ynylidene))fluorene,
(1-methyl(prop-3-ynylidene))cyclopentadiene,
(1-methyl(but-3-ynylidene))cyclopentadiene,
(1-methyl(pent-4-ynylidene))cyclopentadiene,
(1-methyl(hex-5-ynylidene))cyclopentadiene,
(1-methyl(hept-6-ynylidene))cyclopentadiene,
(1-methyl(oct-7-ynylidene))cyclopentadiene,
(1-methyl(non-8-ynylidene))cyclopentadiene,
1-(1-methyl(prop-3-ynylidene))indene,
1-(1-methyl(but-3-ynylidene))indene,
1-(1-methyl(pent4-ynylidene))indene,
1-(1-methyl(hex-5ynylidene))indene,
1-(1-methyl(hept-6-ynylidene))indene
1-(1-methyl(oct-7-ynylidene))indene; and
1-(1-methyl(non-8-ynylidene))indene.

5. A process according to claim 1 wherein the alkynyl ketone compound contains from 4 to 16 carbon atoms.

6. A process according to claim 5 wherein the alkynyl ketone compound is 5-hexyn-2-one.

7. A process according to claim 6 wherein the cyclopentadienyl-type compound is cyclopentadiene.

8. A process according to claim 7 wherein the alkynyl ketone compound and the cyclopentadienyl-type compound are reacted at a temperature in the range of from about −78° C. to about 150° C.

9. An alkynyl fulvene group containing compound represented by the formula

QR wherein Q is a cyclopentadienyl-type group,
wherein R is a hydrocarbyl group containing from 3 to 20 carbon atoms
and is bonded to the cyclopentadienyl-type group by means of a carbon—carbon double bond, and
wherein Q or R contain a terminal alkynyl group;
wherein the cyclopentadienyl-type group is a cyclopentadienyl, substituted cyclopentadienyl, indenyl, substituted indenyl, tetrahydroindenyl, fluorenyl, substituted fluorenyl, or octahydrofluorenyl group, wherein the substituents are hydrocarbyl groups containing from 1 to 20 carbon atoms, alkoxy groups containing from 1 to 12 carbon atoms, silyl groups, alkyl halide groups where the alkyl contains from 1 to 12 carbon atoms, or halide.

10. A fulvene group containing compound according to claim 9 wherein R contains a terminal alkynyl group.

11. An alkynyl fulvene group containing compound according to claim 9 which is 6-(but-3-ynyl)-6-(methyl)fulvene.

12. An alkynyl fulvene group containing compound according to claim 9 wherein said alkynyl fulvene group containing compound is selected from the group consisting of 9-(1-methyl(prop-2-ynylidene))fluorene,
9-(1-methyl(but-3-ynylidene))fluorene,
9-(1-methyl(pent-4-ynylidene))fluorene,
9-(1-methyl(hex-5-ynylidene))fluorene,
9-(1-methyl(hept-6-ynylidene))fluorene,
9-(1-methyl(oct-7-ynylidene))fluorene,
9-(1-methyl(non-8-ynylidene))fluorene,
(1-methyl(prop-3-ynylidene))cyclopentadiene,
(1-methyl(but-3-ynylidene))cyclopentadiene,
(1-methyl(pent-4-ynylidene))cyclopentadiene,
(1-methyl(hex5-ynylidene))cyclopentadiene,
(1-methy(hept-6-ynylidene))cyclopentadiene,
(1-methyl(oct-7-ynylidene))cyclopentadiene,
(1-methyl(non-8-ynylidene))cyclopentadiene,
1-(1-methyl(prop-3-ynylidene))indene,
1-(1-methyl(but-3-ynylidene))indene,
1-(1-methyl(pent-4-ynylidene))indene,
1-(1-methyl(hex-5-ynylidene))indene,
1-(1-methyl(hept-6-ynylidene))indene,
1-(1-methyl(oct-7-ynylidene))indene,
1-(1-methyl(non-8-ynylidene))indene,
9-(isopropylidene)-2-(prop-2-ynyl)fluorene,
9-(isopropylidene)-3-(but-3-ynyl)fluorene,
9-(isopropylidene)-3-(pent-4-ynyl)fluorene,
9-(isopropylidene)-4-(hex-5-ynyl)fluorene,
9-(isopropylidene)-2-(hept-6-ynyl)fluorene,
9-(isopropylidene)-2-(oct-7-ynyl)fluorene,
9-(isopropylidene)-2-(non-8-ynyl)fluorene,
(isopropylidene)-3-(prop-2-ynyl)cyclopentadiene,
(isopropylidene)-3-(but-3-ynyl)cyclopentadiene,
(isopropylidene)-3-(pent4-ynyl)cyclopentadiene,
(isopropylidene)-3-(hex-5-ynyl)cyclopentadiene,
(isopropylidene)-2-(hept-6-ynyl)cyclopentadiene,
(isopropylidene)-2-(oct-7-ynyl)cyclopentadiene,
(isopropylidene)-3-(non-8-ynyl)cyclopentadiene,
1-(isopropylidene)-3-1prop-2-ynyl)indene,
1-(isopropylidene)-3-(but-3-ynyl)indene,
1-(isopropylidene)-3-(pent-4-ynyl)indene,
1-(isopropylidene)-3-(1hex-5-ynyl)indene,
1-(isopropylidene)-2-(hept-6-ynyl)indene,
1-(isopropylidene)-2-(oct-7-ynyl)indene, and
1-(isopropylidene)-3-(non-8-ynyl)indene.

* * * * *

UNITED STATES PATENT AND TRADEMARK OFFICE
CERTIFICATE OF CORRECTION

PATENT NO.   : 5,744,666

DATED        : April 28, 1998

INVENTOR(S)  : M. Bruce Welch, Bernd Peifer and Helmut G. Alt

It is certified that error appears in the above-identified patent and that said Letters Patent is hereby corrected as shown below:

Column 16, claim 12, line 46, delete [3-1] and insert --- 3-(... ---.
Column 16, claim 12, line 49, delete [ 3-(1hex] and insert --- 3-(hex ---.

Signed and Sealed this

Twenty-eighth Day of July, 1998

*Attest:*

BRUCE LEHMAN

*Attesting Officer*      *Commissioner of Patents and Trademarks*